United States Patent
Hayakawa et al.

(10) Patent No.: US 11,872,323 B2
(45) Date of Patent: Jan. 16, 2024

(54) GASIFIER FOR STERILIZER AND CLEANING METHOD OF GASIFIER FOR STERILIZER

(71) Applicant: Dai Nippon Printing Co., Ltd., Tokyo (JP)

(72) Inventors: Atsushi Hayakawa, Tokyo (JP); Masatoshi Takagi, Tokyo (JP); Kazufumi Suzuki, Tokyo (JP); Hidenori Tanaka, Tokyo (JP); Hayato Akiyama, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 17/650,110

(22) Filed: Feb. 7, 2022

(65) Prior Publication Data
US 2022/0152247 A1  May 19, 2022

Related U.S. Application Data

(63) Continuation of application No. 16/478,601, filed as application No. PCT/JP2018/005854 on Feb. 20, 2018, now Pat. No. 11,305,029.

(30) Foreign Application Priority Data

Feb. 20, 2017  (JP) ................. 2017-029250

(51) Int. Cl.
*A61L 2/00* (2006.01)
*A61L 2/20* (2006.01)
*B65B 55/10* (2006.01)
(Continued)

(52) U.S. Cl.
CPC ............. *A61L 2/208* (2013.01); *B65B 55/10* (2013.01); *A01N 59/00* (2013.01); *A23L 3/24* (2013.01);
(Continued)

(58) Field of Classification Search
CPC ............ A61L 2/00; A61L 2/0088; A61L 2/18; A61L 2/186
(Continued)

(56) References Cited

U.S. PATENT DOCUMENTS

| 4,797,255 A | 1/1989 | Hatanaka et al. |
| 2001/0036430 A1* | 11/2001 | Itoh ......................... A61L 2/208 422/305 |
| 2004/0081579 A1 | 4/2004 | Bjerborn |
| 2006/0249182 A1 | 11/2006 | Hayamizu et al. |

(Continued)

FOREIGN PATENT DOCUMENTS

| CN | 1840248 A | 10/2006 |
| CN | 201335368 Y | 10/2009 |

(Continued)

OTHER PUBLICATIONS

International Search Report and Written Opinion (Application No. PCT/JP2018/005854) dated May 22, 2018.
(Continued)

*Primary Examiner* — Monzer R Chorbaji
(74) *Attorney, Agent, or Firm* — BURR PATENT LAW, PLLC

(57) ABSTRACT

A device capable of stably obtaining gas of a sterilizer containing hydrogen peroxide for a long time is provided. A cleaning device that cleans a heating surface that gasifies a sterilizer of a gasifier for a sterilizer is provided, and after an operation for a fixed time period, the heating surface is cleaned.

8 Claims, 6 Drawing Sheets

(51) Int. Cl.
    *A01N 59/00*      (2006.01)
    *A23L 3/24*       (2006.01)
    *A23L 3/3445*     (2006.01)

(52) U.S. Cl.
    CPC ......... *A23L 3/3445* (2013.01); *A61L 2202/23* (2013.01)

(58) Field of Classification Search
    USPC .............................. 422/1, 28, 298, 305, 307
    See application file for complete search history.

(56) References Cited

U.S. PATENT DOCUMENTS

| | | |
|---|---|---|
| 2013/0183196 A1 | 7/2013 | Iwashita et al. |
| 2016/0185584 A1 | 6/2016 | Hayakawa et al. |

FOREIGN PATENT DOCUMENTS

| | | |
|---|---|---|
| CN | 203196964 U | 9/2013 |
| CN | 104755411 A | 7/2015 |
| JP | S60-220067 A1 | 11/1985 |
| JP | S63-011163 A1 | 1/1988 |
| JP | H03-224469 A1 | 10/1991 |
| JP | H06-269602 A1 | 9/1994 |
| JP | H10-218134 A1 | 8/1998 |
| JP | H10-258811 A1 | 9/1998 |
| JP | 2001-502277 A1 | 2/2001 |
| JP | 2006-240969 A1 | 9/2006 |
| JP | 2015-077584 A1 | 4/2015 |
| JP | 2017-024760 A1 | 2/2017 |
| WO | 03/031551 A1 | 4/2003 |
| WO | 2015/008784 A1 | 1/2015 |
| WO | 2016/114273 A1 | 7/2016 |

OTHER PUBLICATIONS

Chinese Offce Action (Application No. 201880008762.2) dated Jul. 2, 2020 (with English translation).
Extended European Search Report (Application No. 18753557.0) dated Nov. 25, 2020.

\* cited by examiner

GASIFIER FOR STERILIZER AND CLEANING METHOD OF GASIFIER FOR STERILIZER

CROSS REFERENCE TO RELATED APPLICATIONS

This application is a continuation of U.S. application Ser. No. 16/478,601, filed Jul. 17, 2019, which in turn is the National Stage entry of International Application No. PCT/JP2018/005854, filed Feb. 20, 2018, the entireties of which are incorporated herein by reference.

FIELD OF THE INVENTION

The present invention relates to a gasifier for a sterilizer that includes a cleaning device, and produces gas of a sterilizer used for sterilization of a packaging in an aseptic filling and packaging machine, and a cleaning method of the gasifier for a sterilizer.

BACKGROUND OF THE INVENTION

Aseptic products produced by filling various foods and drinks in various containers by aseptic filling and packaging machines are distributed, such as creamers, brick carton beverages, pouch soups, cup drinks, and PET-bottled beverages. The aseptic filling and packaging machine is a device that fills a sterilized container with a sterilized content and seals the container in an aseptic atmosphere. Aseptic products produced by the aseptic filling and packaging machine can be distributed at a room temperature and therefore do not have to be refrigerated or frozen, and consume less energy. Further, the aseptic products have little heating histories of the contents, and also taste good, and therefore the aseptic products are increasing.

The aseptic filling and packaging machine handles various types of packaging used as containers as described above, and sterilization processes differ according to the packaging. In some processes, packaging are irradiated with ultraviolet rays or electron beams, but a method of sterilizing surfaces of the packaging with a sterilizer is generally used. When packaging are sterilized by using a sterilizer, packaging which are flat before molding such as creamers or brick cartons are sterilized by being immersed in the sterilizer, but there is also a method for spraying the sterilizer. Packaging that are flat and do not have a problem to a drying temperature at a relatively high temperature after immersion are sterilized by immersion, but molded containers such as cups or bottles or other packaging such as films that are stretched by drying at high temperatures are sterilized by spraying of the sterilizer.

If drops of the sprayed sterilizer are large, the sterilizer can flow down the side surface of the cup or bottle. The smaller the drops of the sprayed sterilizer, the more uniformly the sterilizer is applied to the surface of the packaging, and the higher the sterilization effect is. In this respect, there has been proposed a method of making drops of the sterilizer finer (Patent Literature 1).

The smaller the drops of the sterilizer adhering to the surface of the packaging, and the more densely the surface of the packaging is covered with the drops of the sterilizer, the higher the sterilization effect is. Therefore, instead of a method of spraying the drops of the sterilizer, there has been proposed a method of gasifying the sterilizer, blowing the gas of the sterilizer to the surface of the packaging, and letting the sterilizer condense on the surface of the packaging (Patent Literature 2). The gasification of the sterilizer is achieved by dripping the sterilizer onto a heating element which is heated.

Furthermore, there has also been proposed a method of efficiently gasifying a large amount of sterilizer by spraying the sterilizer into a heated pipe (Patent Literature 3). Furthermore, there has also been proposed a method in which a heat reservoir is provided in the heated pipe (Patent Literature 4).

A hydrogen peroxide solution is mainly used as the sterilizer, and any trace amount of heavy metal contained in the hydrogen peroxide solution causes decomposition of hydrogen peroxide. To prevent this, sodium pyrophosphate or orthophosphoric acid, which has been proven to be safe and effective, is added as a stabilizer to the hydrogen peroxide solution used for sterilization in the aseptic filling and packaging machine (Patent Literature 5). When the hydrogen peroxide solution is gasified, such a stabilizer can be deposited and accumulated on the surface of the heating element, thereby reducing the efficiency of the gasification of the hydrogen peroxide solution or blocking the nozzle that blasts the gas of the hydrogen peroxide solution to the object to be sterilized. To solve the problems with the deposition of the stabilizer, there has been proposed a method of temporarily gasifying the hydrogen peroxide solution, cooling the resulting gas and passing the gas through a filter, and then gasifying the liquefied hydrogen peroxide solution (Patent Literature 6).

CITATION LIST

Patent Literature

Patent Literature 1: Japanese Patent Laid-open No. S60-220067
Patent Literature 2: Japanese Patent Laid-open No. S63-11163
Patent Literature 3: Japanese Patent Laid-open No. H3-224469
Patent Literature 4: Japanese Patent Laid-open No. H10-218134
Patent Literature 5: Japanese Patent Laid-open No. 2006-240969
Patent Literature 6: Japanese Patent Laid-open No. H10-258811

SUMMARY OF THE INVENTION

Technical Problem

To sterilize a packaging in an aseptic filling and packaging machine, a gasified hydrogen peroxide solution is often used. Conventionally, the method for gasifying a hydrogen peroxide solution is achieved by bringing the hydrogen peroxide solution into contact with the heating element. However, if gasification of the hydrogen peroxide solution is performed for a long time period, the stabilizer which is added to the hydrogen peroxide solution can be deposited and accumulated on the heating element as the hydrogen peroxide solution is gasified. The accumulated stabilizer impedes heat conduction to the outermost surface of the heating element, and reduces the efficiency of gasification of the hydrogen peroxide solution. To avoid this, the gasifier for a sterilizer needs to be regularly disassembled and cleaned, which reduces productivity.

To prevent the harmful effects by the deposition of the stabilizer like this, the method disclosed in Patent Literature 6 has been proposed, but in this method, gasification of the hydrogen peroxide solution has to be performed twice, and the stabilizer is not contained in the hydrogen peroxide solution in the second gasification. Therefore, decomposition of the hydrogen peroxide advances, the concentration of hydrogen peroxide in the gas decreases, and as a result, the sterilization effect decreases. In addition, since gasification is conducted twice, the energy consumption is high.

The present invention has been devised to solve the problems described above, and an object of the present invention is to provide a gasifier for a sterilizer that produces gas of a sterilizer containing hydrogen peroxide as a sterilizing component for sterilizing packaging with high concentration, stably for a long time, by preventing accumulation of a stabilizer by cleaning a heating element that gasifies the sterilizer without disassembling the gasifier for a sterilizer, and a cleaning method of the gasifier for a sterilizer.

Solution to Problem

A gasifier for a sterilizer according to the present invention is a device that brings a sterilizer containing at least hydrogen peroxide and a stabilizer into contact with a heating surface to gasify the sterilizer, wherein a cleaning device that cleans the heating surface is provided, and the cleaning device includes a cleaning liquid blasting device that blasts a cleaning liquid to the heating surface.

Further, in the gasifier for a sterilizer according to the present invention, it is preferable that the cleaning device includes a tank that stores the cleaning liquid, a pump that supplies the cleaning liquid to the cleaning liquid blasting device, and an air supplying device that supplies air to the cleaning liquid blasting device.

Further, in the gasifier for a sterilizer according to the present invention, it is preferable that the cleaning liquid blasting device is a one-fluid sprayer.

Further, in the gasifier for a sterilizer according to the present invention, it is preferable that a cleaning liquid circulating device having a discharge port closing cup that closes a cleaning liquid discharge port from which the cleaning liquid is discharged, and recovers the cleaning liquid which is discharged, and a circulation pump that supplies the recovered cleaning liquid to the cleaning device is provided.

Further in the gasifier for a sterilizer according to the present invention, it is preferable that the heating surface has a cylindrical shape.

A cleaning method of a gasifier for a sterilizer according to the present invention is a cleaning method that cleans a gasifier for a sterilizer that brings a sterilizer containing at least hydrogen peroxide and a stabilizer into contact with a heating surface to gasify the sterilizer, wherein the heating surface is cleaned by blasting a cleaning liquid to the heating surface.

Further, in the cleaning method of a gasifier for a sterilizer according to the present invention, it is preferable that the cleaning liquid is water or water containing an acidic compound or a basic compound.

Further, in the cleaning method of a gasifier for a sterilizer according to the present invention, it is preferable that after the cleaning liquid is blasted to the heating surface, air is blasted to the heating surface.

Further, in the cleaning method of a gasifier for a sterilizer according to the present invention, it is preferable that the cleaning liquid discharge port from which the cleaning liquid is discharged is closed, the cleaning liquid which is blasted to the heating surface is recovered, and the recovered cleaning liquid is blasted to the heating surface.

Further, in the cleaning method of a gasifier for a sterilizer according to the present invention, it is preferable that the heating surface has a cylindrical shape.

Advantageous Effects of Invention

According to the gasifier for a sterilizer and the cleaning method of the gasifier for a sterilizer of the present invention, the stabilizer that is contained in the sterilizer and is deposited on the heating surface can be prevented from accumulating on the heating surface when the sterilizer is gasified. As a result, the gasifier for a sterilizer of the present invention can stably produce a gas of a sterilizer that is used in sterilization of packaging and contains at least high concentration of hydrogen peroxide, for a long time. In other words, the gasifier for a sterilizer of the present invention is mounted, and the cleaning method of the gasifier for a sterilizer is carried out, in an aseptic filling and packaging machine that fills the packaging such as a bottle or cup made of paper or plastics as a material, with a beverage or a dairy product, whereby the sterilization power of the packaging in the aseptic filling and packaging machine can be kept stably for a long time.

DETAILED DESCRIPTION OF THE INVENTION

Hereinafter, embodiments of the present invention will be described with reference to the drawings.

First Embodiment

Figure 1:
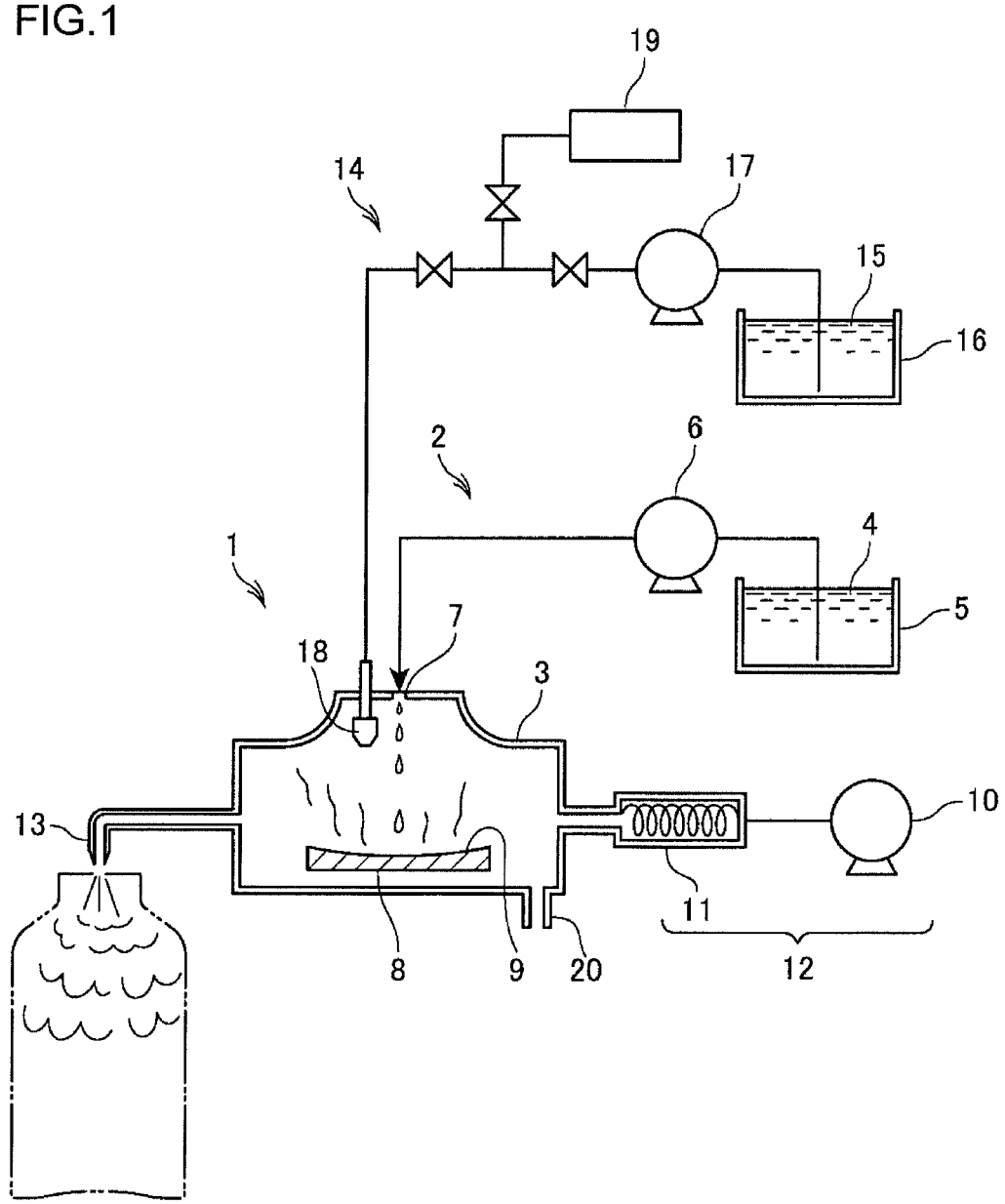
FIG. 1 is a side view of a first embodiment of a gasifier for a sterilizer according to the present invention.

FIG. 1 illustrates a first embodiment of a gasifier 1 for a sterilizer according to the present invention. The gasifier 1 for a sterilizer includes a sterilizer supplying portion 2, a sterilizer evaporating portion 3, and a heated air supplying device 12. The sterilizer supplying portion 2 includes a tank 5 that stores a sterilizer 4, a dropper 7 that drips the sterilizer 4 into the sterilizer evaporating portion 3, and a pump 6 that feeds the sterilizer 4 to the dropper 7. Furthermore, the sterilizer evaporating portion 3 includes a heating body 8 that gasifies the sterilizer 4 dripped into the sterilizer evaporating portion 3. The heated air supplying device 12 includes a blower 10 that feeds air, and a heating device 11 that heats the air fed by the blower 10.

As illustrated in FIG. 1, the sterilizer 4 is dripped onto a heating surface 9 of the heating body 8, and the sterilizer 4 is gasified. The produced gas of the sterilizer 4 is blown from a blowing port 13 by heated air. Packaging is sterilized by the gas of the sterilizer 4 which is blown. A stabilizer contained in the sterilizer 4 is deposited when the sterilizer 4 is gasified on the heating surface 9, and the stabilizer adheres to the heating surface 9.

In order to remove the stabilizer adhering to the heating surface 9, a cleaning device 14 that cleans the heating surface 9 is provided at the gasifier 1 for a sterilizer. The cleaning device 14 includes a cleaning liquid blasting device 18 that blasts a cleaning liquid 15 to the heating surface 9. Further, the cleaning device 14 includes a cleaning liquid tank 16 that stores the cleaning liquid 15, a pump 17 that supplies the cleaning liquid 15 to the cleaning liquid blasting device 18, and an air supplying device 19 that supplies air that is blasted to the sterilizer evaporating portion 3 to remove the cleaning liquid 15 from an inside of the sterilizer evaporating portion 3.

The sterilizer 4 contains at least hydrogen peroxide. The content of the hydrogen peroxide is appropriately in a range of 0.5% by mass to 65% by mass. If the content is lower than 0.5% by mass, the sterilizing power can be insufficient, whereas if the content is higher than 65% by mass, it is difficult to safely handle the sterilizer 4. A more preferable range is 0.5% by mass to 40% by mass. If the content is equal to or lower than 40% by mass, the sterilizer 4 can be more easily handled, and the amount of the hydrogen peroxide remaining on the packaging after sterilization can be reduced because of the low concentration.

Further, the sterilizer 4 also contains a stabilizer to prevent decomposition of hydrogen peroxide. It is preferable that the stabilizer contained in the sterilizer 4 is sodium pyrophosphate or orthophosphoric acid which is used as a food additive for food products specified by the Minister of Health, Labor and Welfare to sterilize packaging for food. However, an inorganic compound containing phosphorous such as sodium hydrogen pyrophosphate, a phosphonate chelating agent such as aminotrimethylphosphonic acid alkylidenediphosphonate, or the like may also be used. The content of the stabilizer is typically equal to or lower than 40 ppm.

Although the sterilizer 4 contains water, the sterilizer 4 may contain one or more of alcohols such as methyl alcohol, ethyl alcohol, isopropyl alcohol, normal propyl alcohol and butyl alcohol, ketones such as acetone, methyl ethyl ketone and acetylacetone, and glycol ethers, for example.

Further, the sterilizer 4 may further contain an additive agent such as a compound having a sterilizing effect such as peracetic acid, acetic acid, a chlorine compound or ozone, a cationic surface active agent and a non-ionic surface active agent.

The sterilizer 4 stored in the tank 5 is supplied to the dropper 7 by the pump 6, the supply amount is arbitrary, and the sterilizer 4 is supplied based on the required amount of the gas of the sterilizer 4. When the gas of the sterilizer 4 to be supplied is insufficient with the one dropper 7, a plurality of droppers 7 is used. The amount of the sterilizer dripped by the dropper 7 is also determined based on the required amount of the gas of the sterilizer, and the amount of the gas produced on the heating surface 9 is determined by the temperature and heat capacity of the heating body 8.

The temperature of the heating surface 9 of the heating body 8 that gasifies the sterilizer 4 is set at 130° C. to 450° C. If the temperature is lower than 130° C., gasification is difficult, whereas if the temperature is higher than 450° C., hydrogen peroxide is decomposed. Further, the heating surface 9 of the heating body 8 may be a planar surface, and horizontal or provided with an inclination, or may be a curved surface such as a concave or convex surface. The heating surface 9 of the heating body 8 can have any shape as far as the sterilizer 4 can come into contact with the heating surface 9 of the heating body 8 and be gasified. The heating body 8 can have any size and thickness. When the volume of the heating body 8 is large, the heat capacity is large, which is advantageous for gasification of the sterilizer 4, but the gasifier 1 for a sterilizer becomes excessively large.

For the heating body 8, a metal such as iron, stainless steel, a copper alloy, aluminum, an aluminum alloy, zinc or tungsten is used. In general, stainless steel having resistance to hydrogen peroxide, such as SUS304, SUS316 or SUS316L is used.

The heating surface 9 of the heating body 8 may be made of chrome. The material of the heating body 8 itself may be chromium and the heating body 8 may be made of iron, stainless steel, a copper alloy, aluminum, an aluminum alloy, zinc, or tungsten, and the surface of the heating body 8 may be plated with chromium. An outermost surface of the chromium reacts with oxygen to form chromium oxide, which is passive, the outermost surface is extremely stable and does not corrode for a long time even though the hydrogen peroxide contained in the sterilizer 4 at a high temperature comes into contact with the surface.

When the surface of the heating body 8 is plated with chromium, the thickness of the plating is appropriately 0.1 µm to 100 µm. Before the plating, the material to be plated may be plated with copper or nickel. The surface of the chromium which is plated may be polished to improve the smoothness.

It is estimated that the heating surface 9 which is the surface of the heating body 8 is made of chromium, whereby decomposition of hydrogen peroxide is reduced when the hydrogen peroxide contained in the sterilizer 4 is gasified, and therefore, the amount of hydrogen peroxide contained in the gas of the sterilizer 4 produced by the gasifier 1 for a sterilizer becomes larger as compared with the heating surface 9 made of stainless steel or the like as in the prior art.

The surface of the heating surface 9 preferably has an arithmetic mean roughness (Ra) of 1.0 µm or less and a ten-point mean roughness (Rz) of 2.0 µm or less. If Ra is greater than 1.0 µm, or Rz is greater than 2.0 µm, the concentration of hydrogen peroxide in the gas of the sterilizer decreases. It is presumed that this is because if the surface area is large, the sterilizer is excessively heated when the sterilizer comes into contact with the heating surface 9 and is gasified, and thereby hydrogen peroxide is easily decomposed.

The heating surface 9 of the heating body 8 may be made of polytetrafluoroethylene or perfluoroalkoxy fluorocarbon resin, or chromium plating impregnated with polytetrafluoroethylene or perfluoroalkoxy fluorocarbon resin. The heating surface 9 is made of polytetrafluoroethylene or perfluoroalkoxy fluorocarbon resin, or a chromium plating impregnated with polytetrafluoroethylene or perfluoroalkoxy fluorocarbon resin, whereby the anti-stick quality of the heating surface 9 can reduce adherence of the stabilizer to the heating surface 9, which is deposited when the sterilizer 4 comes into contact with the heating surface 9 and is gasified. As a result, the number of cleaning times of the heating surface 9 can be reduced.

Polytetrafluoroethylene is a polymer of the monomer tetrafluoroethylene, and has a melting point of about 325° C. The perfluoroalkoxy fluorocarbon resin is a copolymer of tetrafluoroethylene and perfluoroether, and has a melting point of about 310° C. The surface of the heating body 8 is subjected to a surface treatment such as degreasing, blasting or high-pressure blasting with ceramic particles in order to enhance adhesion, and thereafter the surface of the heating body 8 is coated by a method such as electrostatic powder coating. Further, the heating body 8 coated with polytetrafluoroethylene or perfluoroalkoxy fluorocarbon resin is baked at about 400° C., and thereby the heating surface 9 is formed. The coating and baking may be conducted twice or more times. The thickness of the polytetrafluoroethylene or perfluoroalkoxy fluorocarbon resin is desirably 100 μm to 1000 μm. If the thickness is less than 100 μm, pin holes can occur, whereas if the thickness is greater than 1000 μm, heat conduction from the heating body 8 is compromised.

When the chromium plating impregnated with polytetrafluoroethylene or perfluoroalkoxy fluorocarbon resin is formed on the surface of the heating body 8, the thickness of the plating is appropriately 1 μm to 100 μm. Before the plating, the material to be plated may be plated with copper or nickel. The surface of the chromium which is plated may be polished to improve the smoothness.

As for a method for heating the heating body 8, as far as the heating body 8 can be heated to a desired temperature, any method may be adopted, such as passing a current to the heating body 8 to make the heating body 8 itself generate heat, embedding a heater in the heating body 8, placing the heating body 8 in contact with a heater, or heating the heating body 8 with an induction heating device. Further, warm water or steam may be supplied to inside of the heating body 8.

The gas of the sterilizer 4 produced in the sterilizer evaporating portion 3 is discharged through the blowing port 13 by the heated air fed from the heated air supplying device 12 and is used to sterilize a packaging such as a bottle. Any amount of heated air can be supplied, but as the amount of the supplied heated air increases, the concentration of hydrogen peroxide contained in the gas of the sterilizer 4 decreases, and the sterilizing power can be poor. Further, as the amount of the supplied heated air is small, the blowing pressure of the gas of the sterilizer 4 to the packaging can be low. The temperature of the heated air is set at 90° C. to 350° C. If the temperature is lower than 90° C., there is a risk that the gasified sterilizer 4 may be liquefied before being used for sterilization, so that the covered surface area of the object to be sterilized decreases, and the sterilization effect deteriorates. It is desirable that the gas of the sterilizer 4 comes into contact with the object to be sterilized, the gas of the sterilizer 4 condenses to form fine mist on the object, and the temperature of the heated air is set at an appropriate temperature for achieving this. As the temperature of the heated air is higher than 350° C., some objects to be sterilized can be deformed. Some objects to be sterilized can be deformed at a temperature lower than 350° C., and therefore this should be kept in mind.

The diameter of the blowing port 13 for the gas of the sterilizer 4 can be arbitrarily set and can be set at 2 mmϕ to 200 mmϕ, for example. By making the diameter small, the blowing pressure of the produced gas of the sterilizer 4 can be increased. By adjusting the blowing pressure, the intensity of blowing of the gas of the sterilizer 4, the mist generated by condensation of the sterilizer gas, or a mixture thereof onto the surface of the object to be sterilized can be adjusted. For example, if the object to be sterilized is a deep cup, the sterilizer gas and the like can be blown with high intensity, whereas if the object to be sterilized is a shallow container, the sterilizer and the like can be blown with low intensity. If the blowing port 13 is long, the gas of the sterilizer 4 may be cooled and condense, and therefore, the periphery of the blowing port 13 may be heated.

When the gasifier 1 for a sterilizer is operated for a fixed time period, the stabilizer is deposited on the heating surface 9. In order to remove the deposited stabilizer, the cleaning liquid 15 is blasted to the heating surface 9 from the cleaning liquid blasting device 18. The cleaning liquid 15 is supplied to the cleaning liquid blasting device 18 by the pump 17 from the cleaning liquid tank 16.

The cleaning liquid 15 is water, or water containing an acidic compound or a basic compound. Water is water sterilized by heating or filtration, pure water, ion exchanged water, distilled water, tap water or the like. The acidic compound is an inorganic acid such as hydrochloric acid, nitric acid, or phosphoric acid, or an organic acid such as acetic acid, formic acid, oxalic acid, citric acid, succinic acid, or gluconic acid. Further, the basic compound is an inorganic basic compound such as sodium hydroxide, or potassium hydroxide, or an organic basic compound such as ethanolamine or diethylamine. In addition to the above, the cleaning liquid 15 may contain alkali metal salt of an organic acid, alkaline earth metal salt, ammonium salt, hydroxycarboxylic acid compound such as alkanolamine salt of ethylenediaminetetraacetic acid or the like, a sequestering agent, an anionic surfactant, a cationic surfactant, a nonionic surfactant such as polyoxyethylene alkyl phenyl ethers, a solubilizer such as sodium cumene sulfonate, an acid based polymer such as polyacrylic acid or metal salt of acid based polymers, a corrosion inhibiter, a preservative, an antioxidant, a dispersant, a defoamer or the like.

The cleaning liquid is prepared by dissolving 0.001% by mass to 30% by mass of an acidic compound or a basic compound into water. When water or aseptic water containing an acidic compound, basic compound or the other additive is used as the cleaning liquid 15, it is necessary to blast water or aseptic water to the heating surface 9 as the cleaning liquid 15 to remove the acidic compound, the basic compound or the other additive after the water or the aseptic water containing the acidic compound, the basic compound or the other additive is blasted to the heating surface 9.

The cleaning liquid blasting device 18 is, for example, a one-fluid sprayer, pressure of 0.05 to 0.6 MPa is added to the cleaning liquid 15 by the pump 17, and the cleaning liquid 15 is blasted to the heating surface 9 by the cleaning liquid blasting device 18 which is the one-fluid sprayer. By the pressure of the cleaning liquid 15 which is blasted, the deposited stabilizer is removed from the heating surface 9. Further, the deposited stabilizer is removed by being dissolved in or reacting with the cleaning liquid 15.

The deposited stabilizer is sodium pyrophosphate or orthophosphoric acid contained in hydrogen peroxide. Further, the deposited stabilizer is an inorganic compound containing phosphorous such as sodium hydrogen pyrophosphate or a phosphonate chelating agent such as aminotrimethylphosphonic acid alkylidenediphosphonate, and iron pyrophosphate in which the stabilizer is bound to a metal ion such as iron, or the like is also included.

When the cleaning liquid 15 is blasted to the heating surface 9, the temperature of the heating body 8 is preferably 50° C. to 250° C. The temperature is more preferably 60° C. to 200° C. This is because the higher the temperature of the heating body 8, the higher the cleanability. The cleaning liquid 15 may be blasted to the heating surface 9 when the aseptic filling and packaging machine loaded with the gasifier 1 for a sterilizer is not operating. The cleaning liquid 15 may be blasted to the heating surface 9 periodically, such as once a year, once a month or once a week. However, it is more preferable to carry out the blasting directly after the product is produced by using the aseptic filling and packaging machine, because the stabilizer is efficiently removed.

The cleaning liquid 15 which is blasted to the heating surface 9 is discharged from the cleaning liquid discharge port 20 provided in a lower part of the sterilizer evaporating portion 3 of the gasifier 1 for a sterilizer. Further, in order to discharge the cleaning liquid 15 remaining inside the sterilizer evaporating portion 3 completely after the cleaning liquid 15 is blasted to the heating surface 9, air is supplied to the cleaning liquid blasting device 18 from the air supplying device 19, and air is blasted to the heating surface 9. Air is pressurized air having a pressure of 0.01 MPa to 1.0 MPa, for example. A device that pressurizes air in the air supplying device 19 may be a blower, or a compressor. A blower and a compressor may be used in combination. Further, the pressurized air may be sterilized air. It is effective to repeat blasting of the cleaning liquid 15 and blasting the pressurized air to the heating surface 9 alternately a plurality of times.

Figure 2:
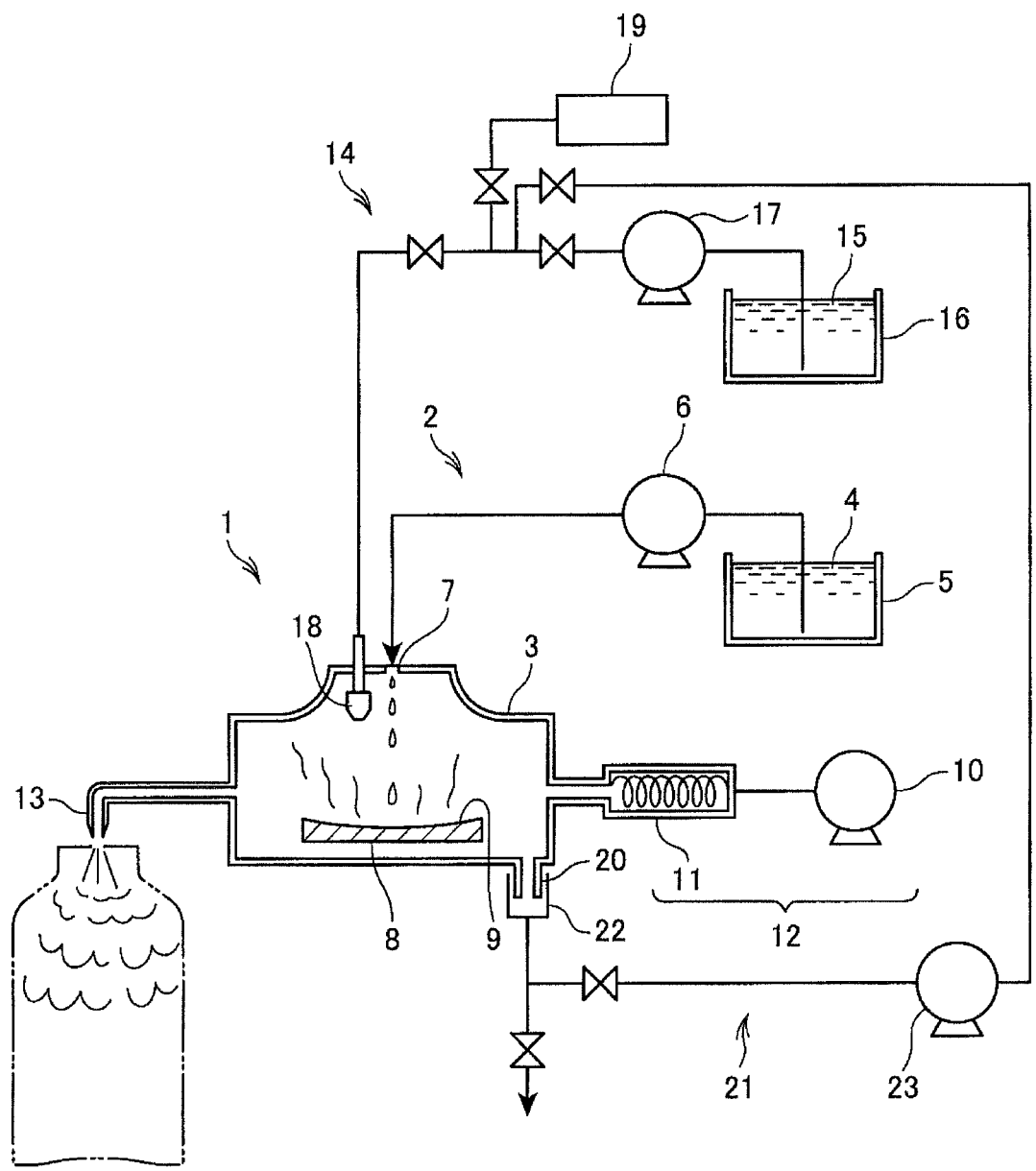
FIG. 2 is a side view of the gasifier for a sterilizer of the first embodiment including a cleaning liquid circulating device according to the present invention.

The cleaning liquid 15 which is discharged from the cleaning liquid discharge port 20 may be directly discarded. However, as illustrated in FIG. 2, a cleaning liquid circulating device 21 is provided so that the cleaning liquid 15 which is blasted to the heating surface 9 can be recovered and the recovered cleaning liquid 15 can also be blasted to the heating surface 9. The cleaning liquid circulating device 21 includes a discharge port closing cup 22 for closing the cleaning liquid discharge port 20, and recovering the cleaning liquid 15, and a circulation pump 23 that circulates the recovered cleaning liquid 15 to the cleaning device 14. A balance tank may be provided between the cleaning liquid discharge port 20 and the circulation pump 23.

The cleaning liquid discharge port 20 is closed with the discharge port closing cup 22, all of the cleaning liquid 15 which is discharged is recovered and pressurized by the circulation pump 23, and the recovered cleaning liquid 15 is circulated into the flow path for the cleaning liquid 15. The recovered cleaning liquid 15 which is circulated is blasted to the heating surface 9 again by the cleaning liquid blasting device 18. In this case, the recovered cleaning liquid 15 may be introduced into the cleaning liquid tank 16, and after the recovered cleaning liquid 15 is stored in the cleaning liquid tank 16, the recovered cleaning liquid 15 may be supplied to the cleaning liquid blasting device 18.

After the cleaning liquid 15 which is recovered by the cleaning liquid circulating device 21 is blasted to the heating surface 9, it is necessary to blast water or aseptic water to the heating surface 9 as the cleaning liquid 15, detach the discharge port closing cup 22 from the cleaning liquid discharge port 20, and discard the cleaning liquid 15. This is for removing the stabilizer, the acidic compound or the basic compound, and the other additives from the inside of the sterilizer evaporating portion 3.

Second Embodiment

Figure 3:
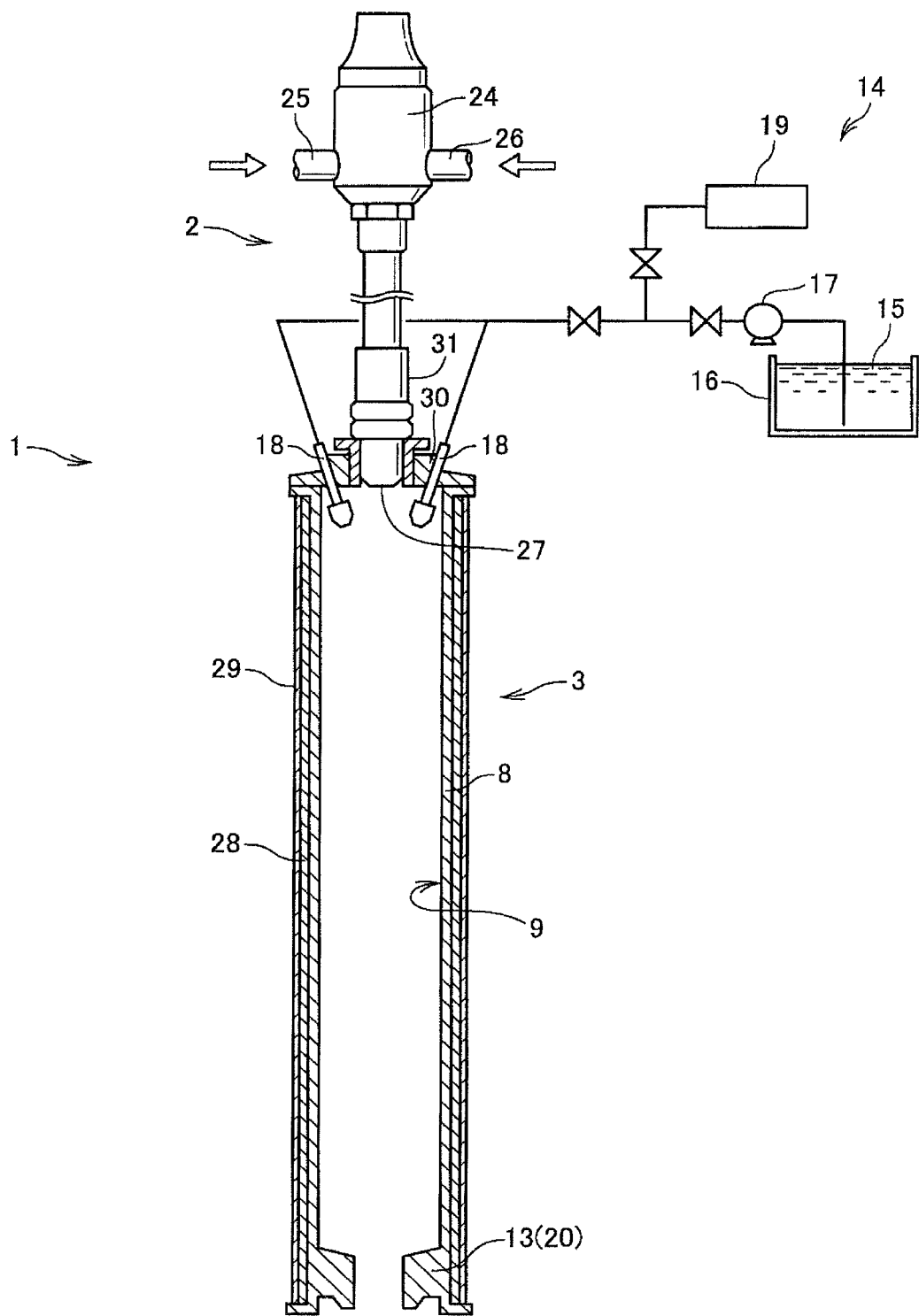
FIG. 3 is a side view illustrating a second embodiment of the gasifier for a sterilizer according to the present invention.

FIG. 3 illustrates a second embodiment of the gasifier 1 for a sterilizer according to the present invention. The gasifier 1 for a sterilizer includes the sterilizer supplying portion 2 and the sterilizer evaporating portion 3. The sterilizer supplying portion 2 includes a spraying device 24, and the spraying device 24 supplies the sterilizer 4 to the sterilizer evaporating portion 3. An inner surface of the sterilizer evaporating portion 3 is formed as the heating body 8. The sterilizer 4 is supplied to the sterilizer supplying portion 2 from a tank not illustrated.

The sterilizer 4 from the sterilizer supplying portion 2 is supplied to a sterilizer supply port 25 of the spraying device 24, and compressed air is supplied to a compressed air supply port 26. The spraying device 24 is a twin-fluid sprayer, and sprays the sterilizer 4 in the form of a mist to the inner surface of the sterilizer evaporating portion 3 from a spray nozzle 27 through an extension pipe 31. The sprayed sterilizer 4 comes into contact with the heating surface 9 of the heating body 8 and is gasified. The extension pipe 31 is provided to prevent the heat of the sterilizer evaporating portion 3 from being conducted to the spraying device 24 through a plug 30 that closes an upper portion of the sterilizer evaporating portion 3 and increasing the temperature of the spraying device 24. The gasified sterilizer 4 is discharged from the gas blowing port 13, and is blown to a packaging to sterilize the packaging. The diameter of the blowing port 13 for the gas of the sterilizer 4 can be set arbitrarily as in the first embodiment.

The sterilizer 4, the materials of the heating body 8 and the heating surface 9 and the like used in the second embodiment are the same as those in the first embodiment. The second embodiment differs from the first embodiment in that the sterilizer is supplied to the sterilizer evaporating portion 3 by spraying a mist of the sterilizer, the heating body 8 forms the inner surface of the sterilizer evaporating portion 3 and has a cylindrical shape, and the heated air supplying device 12 is not included.

The inner surface of the sterilizer evaporating portion 3 forms the heating body 8 in the cylindrical shape, a heater 28 for heating the heating body 8 is provided on an outer surface of the sterilizer evaporating portion 3, and outer covering 29 is further provided on an outer surface of the heater 28 to provide heat insulating properties and protect the heater 28. While FIG. 3 shows that the heater 28 heats the heating body 8, a heating method of the heating body 8 may be any heating method as in the first embodiment.

With regard to operating conditions of the spraying device 24, the pressure of the compressed air is adjusted within a range of 0.05 MPa to 0.6 MPa, for example. Further, the sterilizer 4 may be supplied by gravity or under pressure using the pump 6, the supply amount of the sterilizer 4 can be arbitrarily set, and the sterilizer is supplied at a rate within a range of 1 g/min to 100 g/min, for example.

The sterilizer 4 is sprayed in a circular pattern through the spray nozzle 27, and therefore the heating body 8 preferably has a circular cylindrical shape. However, the heating body 8 may have a polygonal cylindrical shape. A diameter of the cylinder needs to be sufficiently large to prevent the internal pressure of the sterilizer evaporating portion 3 from being increased by the compressed air used to spray the sterilizer 4. For example, the diameter of the cylinder can be set to be 1 mmϕ to 1000 mmϕ. On the other hand, the diameter has to be such a diameter that the sprayed mist of the sterilizer 4 comes into contact with the heating surface 9. Further, the length of the cylinder is also designed so as to meet the conditions.

When the gasifier 1 for a sterilizer is operated for a fixed time period, the stabilizer contained in the sterilizer 4 is deposited and accumulated on the heating surface 9 of the heating body 8. In order to clean the heating surface 9 to remove the deposited stabilizer, the cleaning device 14 for cleaning the heating surface 9 is provided in the gasifier 1 for a sterilizer of the second embodiment as in the first embodiment, as illustrated in FIG. 3.

The cleaning device 14 includes the cleaning liquid blasting device 18. Further, the cleaning device 14 includes the cleaning liquid tank 16 that stores the cleaning liquid 15 to be blasted to the heating surface 9, the pump 17 that supplies the cleaning liquid 15 to the cleaning liquid blasting device 18, and the air supplying device 19 that supplies air to the cleaning liquid blasting device 18 to remove the cleaning liquid 15 from the inside of the sterilizer evaporating portion 3.

The cleaning liquid 15 is blasted to the heating surface 9 that forms the inner surface of the sterilizer evaporating portion 3 from the cleaning liquid blasting device 18. The blasted cleaning liquid 15 is discharged from the blowing port 13. In the second embodiment, the blowing port 13 also functions as the cleaning liquid discharge port 20. Although the two cleaning liquid blasting devices 18 are shown in FIG. 3, only the one cleaning liquid blasting device 18 may be used, if the one cleaning liquid blasting device 18 can clean the heating surface 9. Further, three or more cleaning liquid blasting devices 18 may be used if necessary.

The cleaning liquid 15 similar to that in the first embodiment is used. Further, when water or aseptic water containing an acidic compound, basic compound or other additives is used as the cleaning liquid 15, it is also necessary to blast the water or aseptic water to the heating surface 9 as the cleaning liquid 15 to remove the acidic compound or the basic compound from the inside of the sterilizer evaporating portion 3 after the cleaning liquid is blasted to the heating surface 9 as in the first embodiment.

The cleaning liquid blasting device 18 is a one-fluid sprayer, for example, the pump 17 adds a pressure of 0.05 MPa to 0.6 MPa to the cleaning liquid 15, and the cleaning liquid blasting device 18 which is the one-fluid sprayer blasts the cleaning liquid 15 to the heating surface 9. The pressure of the blasted cleaning liquid 15 removes the deposited stabilizer from the heating surface 9. Further, the stabilizer is dissolved into the cleaning liquid 15, or the stabilizer reacts with the acidic compound or the basic compound contained in the cleaning liquid 15, and thereby the stabilizer adhering to the heating surface 9 is removed.

The cleaning liquid 15 which is blasted to the heating surface 9 is discharged from the blowing port 13 provided in the lower part of the sterilizer evaporating portion 3 of the gasifier 1 for a sterilizer, which also functions as the cleaning liquid discharge port 20. In order to completely discharge the cleaning liquid 15 remaining inside the sterilizer evaporating portion 3 after the cleaning liquid 15 is blasted to the heating surface 9, air is supplied to the cleaning liquid blasting device 18 from the air supplying device 19 included in the cleaning device 14, and is blasted to the heating surface 9. As the air, pressurized air having a pressure of 0.1 MPa to 1.0 MPa is used.

A cleaning step is as follows. After the operation of the gasifier 1 for a sterilizer is stopped, and the temperature of the heating body 8 decreases, the cleaning liquid 15 is blasted to the heating surface 9 for a fixed time period by the cleaning liquid blasting device 18, and thereafter, the blasting is stopped. After the temperature of the heating body 8 decreases to a room temperature, blasting of the cleaning liquid 15 to the heating surface 9 may be started, and the temperature of the heating body 8 is preferably 50° C. to 250° C. The temperature of the heating body 8 is more preferably 60° C. to 150° C. The higher the temperature of the heating body 8, the higher the cleanability, which is preferable. However, when the temperature of the heating body 8 becomes higher than 250° C., the cleaning liquid 15 is gasified, and the internal pressure of the sterilizer evaporating portion 3 increases.

After a fixed time period elapses after stopping blasting of the cleaning liquid 15, the cleaning liquid 15 is blasted for a fixed time period again, and the blasting is stopped. This is repeated several times, and further, air is blasted into the sterilizer evaporating portion 3 for a fixed time period by the cleaning liquid blasting device 18, and the cleaning liquid 15 is removed from the inside of the sterilizer evaporating portions 3. If the diameter of the blowing port 13 which also functions as the cleaning liquid discharge port 20 is taken into consideration, and the cleaning liquid 15 is blasted in a flow amount that fills the inside of the sterilizer evaporating portion 3 with the cleaning liquid 15, it becomes possible to clean the sterilizer evaporating portion 3 up to a top surface of an upper portion of the sterilizer evaporating portion 3. Thereafter, the temperature of the heating body 8 is increased, and when the temperature of the heating body 8 reaches a set temperature, the sterilizer 4 is sprayed into the sterilizer evaporating portion 3 by the spraying device 24 for a fixed time period. Thereafter, an operation of the gasifier 1 for a sterilizer is started.

Figure 4:
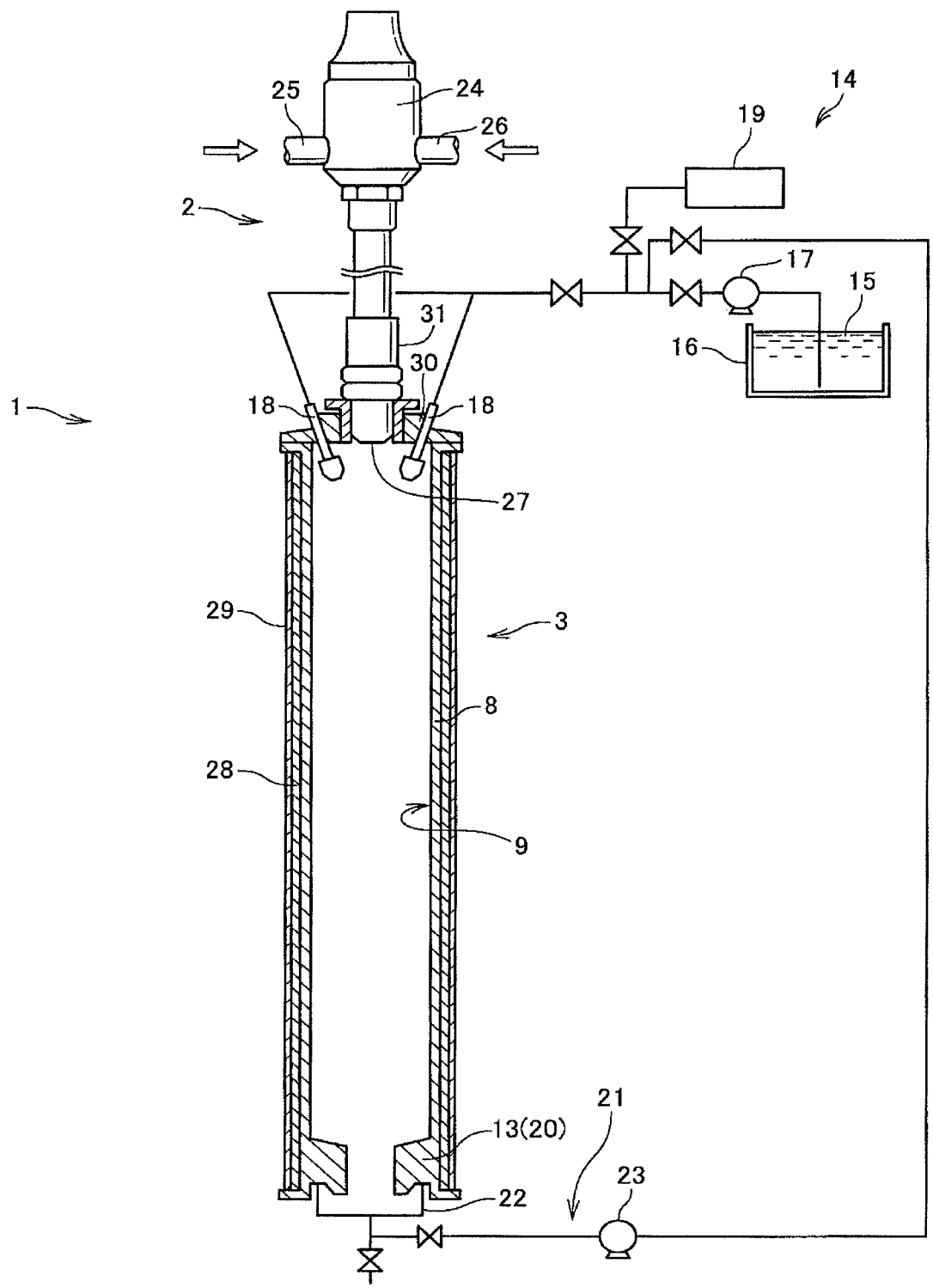
FIG. 4 is a side view illustrating the gasifier for a sterilizer of the second embodiment including a cleaning liquid circulating device, according to the present invention.

The cleaning liquid 15 which is discharged from the cleaning liquid discharge port 20 may be directly discarded. However, as illustrated in FIG. 4, the cleaning liquid circulating device 21 is provided so that the cleaning liquid 15 which is blasted to the heating surface 9 can be recovered and the recovered cleaning liquid 15 can also be blasted to the heating surface 9, as in the first embodiment. The cleaning liquid circulating device 21 includes the discharge port closing cup 22 for closing the blowing port 13 which is the cleaning liquid discharge port 20, and recovering the cleaning liquid 15, and the circulation pump 23 that circulates the recovered cleaning liquid 15. A balance tank may be provided between the blowing port 13 which also functions as the cleaning liquid discharge port 20 and the circulation pump 23.

The cleaning liquid discharge port 20 may be closed with the discharge port closing cup 22, all of the cleaning liquid 15 which is discharged may be recovered, and pressurized by the circulation pump 23, and the recovered cleaning liquid 15 may be introduced into the flow path for the cleaning liquid 15. The recovered cleaning liquid 15 which is introduced is blasted to the heating surface 9 again by the cleaning liquid blasting device 18. In this case, the recovered cleaning liquid 15 may be introduced into the cleaning liquid tank 16, and after the recovered cleaning liquid 15 is stored in the cleaning liquid tank 16, the recovered cleaning liquid 15 may be supplied to the cleaning liquid blasting device 18.

After the cleaning liquid 15 which is recovered by the cleaning liquid circulating device 21 is blasted to the heating surface 9, water or aseptic water is blasted to the heating surface 9 as the cleaning liquid 15. At this time, the discharge port closing cup 22 has to be detached from the blowing port 13, and the cleaning liquid 15 has to be discarded. This is for removing the stabilizer, the acidic compound, the basic compound, and the other additives from the inside of the sterilizer evaporating portion 3. Further, while the gasifier 1 for a sterilizer is operating, the gas of the sterilizer 4 is blown to packaging from the blowing port 13, and therefore the discharge port closing cup 22 is detached and is held so as not to interfere with the operation.

Although in the second embodiment, the cleaning liquid 15 is blasted to the heating surface 9 from the cleaning liquid blasting device 18, the cleaning liquid 15 may be supplied to the spraying device 24 from the sterilizer supply port 25, and the cleaning liquid 15 may be blasted into the sterilizer evaporating portion 3 from the spray nozzle 27. In this case, the cleaning liquid 15 is stored in the cleaning liquid tank 16, and is supplied to the sterilizer supply port 25 by the pump 17. The spraying device 24 is equipped with the compressed air supply port 26, and does not need the air supplying device 19. In other words, after the cleaning liquid 15 is blasted to the heating surface 9 from the spray nozzle 27, the compressed air which is supplied to the spraying device 24 from the compressed air supply port 26 is blasted to the heating surface 9 from the spray nozzle 27, and the cleaning liquid 15 which remains in the sterilizer evaporating portion 3 is removed.

An inside of the extension pipe 31 is not cleaned by the cleaning liquid blasting device 18. The heat of the heating body 8 is conducted to the extension pipe 31, a temperature in a vicinity of the heating body 8 increases, and the stabilizer contained in the sterilizer is likely to be deposited. The inside of the extension pipe 31 may be cleaned by being supplied with the cleaning liquid 15 from the sterilizer supply port 25. In order to increase cleanability, an inside diameter of the extension pipe 31 is preferably 3 mmφ or more.

Third Embodiment

Figure 5:
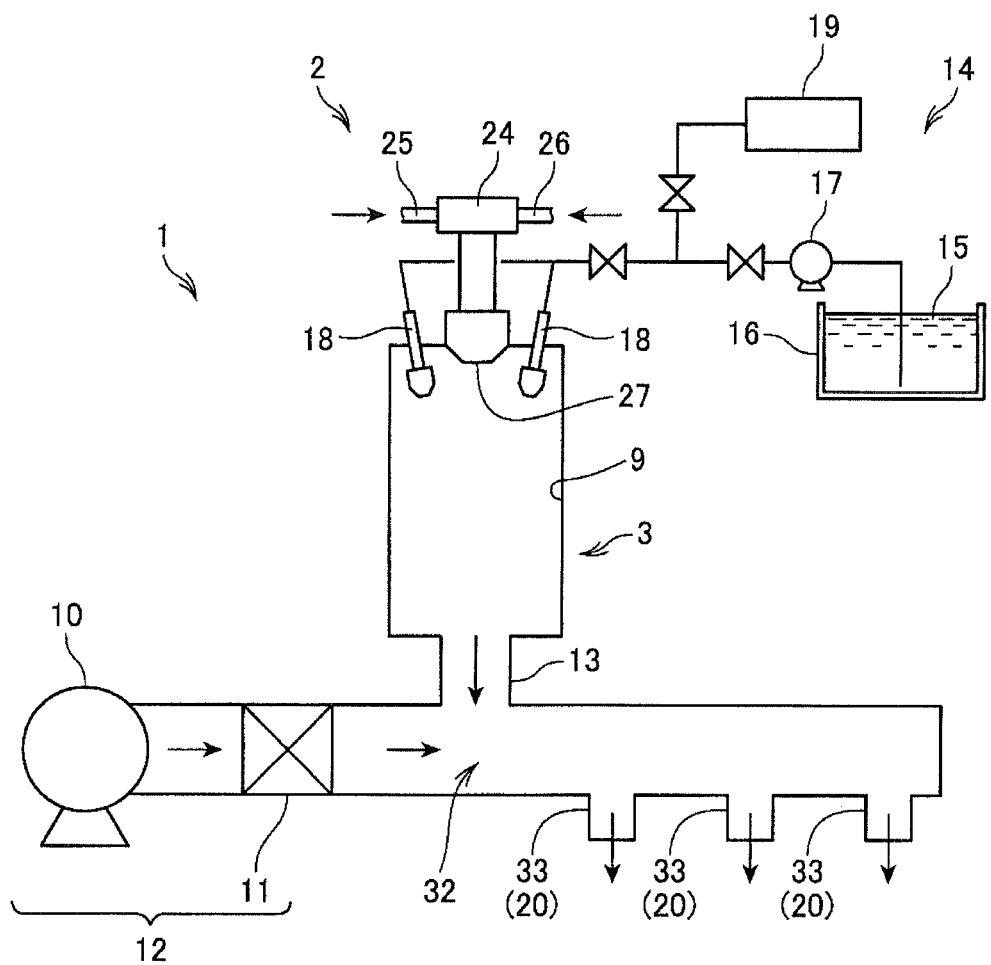
FIG. 5 is a side view illustrating a third embodiment of the gasifier for a sterilizer according to the present invention.

FIG. 5 illustrates a third embodiment of the gasifier 1 for a sterilizer according to the present invention. The sterilizer 4 and the cleaning liquid 15 which are similar to those in the first embodiment are used. Further, for gasification of the sterilizer 4, the gasifier 1 for a sterilizer similar to that of the second embodiment is used, and is operated as in the second embodiment.

The sterilizer 4 which is gasified by the sterilizer evaporating portion 3 is discharged from the blowing port 13 by pressure of the compressed air. The blowing port 13 is caused to face an object to be sterilized, and the gas of the sterilizer 4 to be discharged can be directly blown to a packaging which is the object to be sterilized. However, as illustrated in FIG. 5, the heated air supplying device 12 that introduces heated air is included in an end portion of the sterilizer evaporating portion 3, the gas of the sterilizer 4 which is discharged from the blowing port 13 and the heated air may be mixed in a conduit pipe 32, and the mixed gas may be blown to the packaging from a sterilizer gas blowing port 33. The heated air supplying device 12 includes a blower 10 and a heating device 11, and heats the air by the blower 10 by the heating device 11.

A plurality of sterilizer evaporating portions 3 of the gasifier 1 for a sterilizer may be connected to the conduit pipe 32 instead of the one sterilizer evaporating portion 3. Further, the number of sterilizer gas blowing ports 33 may be one or more. The air is heated to 130° C. to 300° C. by the heating device 11. The temperature of the heated air is set similarly to the first embodiment. A sanitary valve is preferably provided downstream of the heating device 11 so that the cleaning liquid 15 does not flow backward.

After the gasifier 1 for a sterilizer is operated for a fixed time period, the cleaning liquid 15 is blasted to the inner surface of the sterilizer evaporating portion 3 by the cleaning liquid blasting device 18 to clean the heating surface 9, and the cleaning liquid 15 is discharged from the sterilizer gas blowing port 33 which also functions as the cleaning liquid discharge port 20. After the cleaning liquid 15 is blasted to the heating surface 9, the pressurized air which is supplied from the air supplying device 19 is blasted to the heating surface 9 to completely discharge the cleaning liquid 15 which remains inside the sterilizer evaporating portion 3. As for the air pressure, the pressurized air of 0.1 MPa to 1.0 MPa is used.

Figure 6:
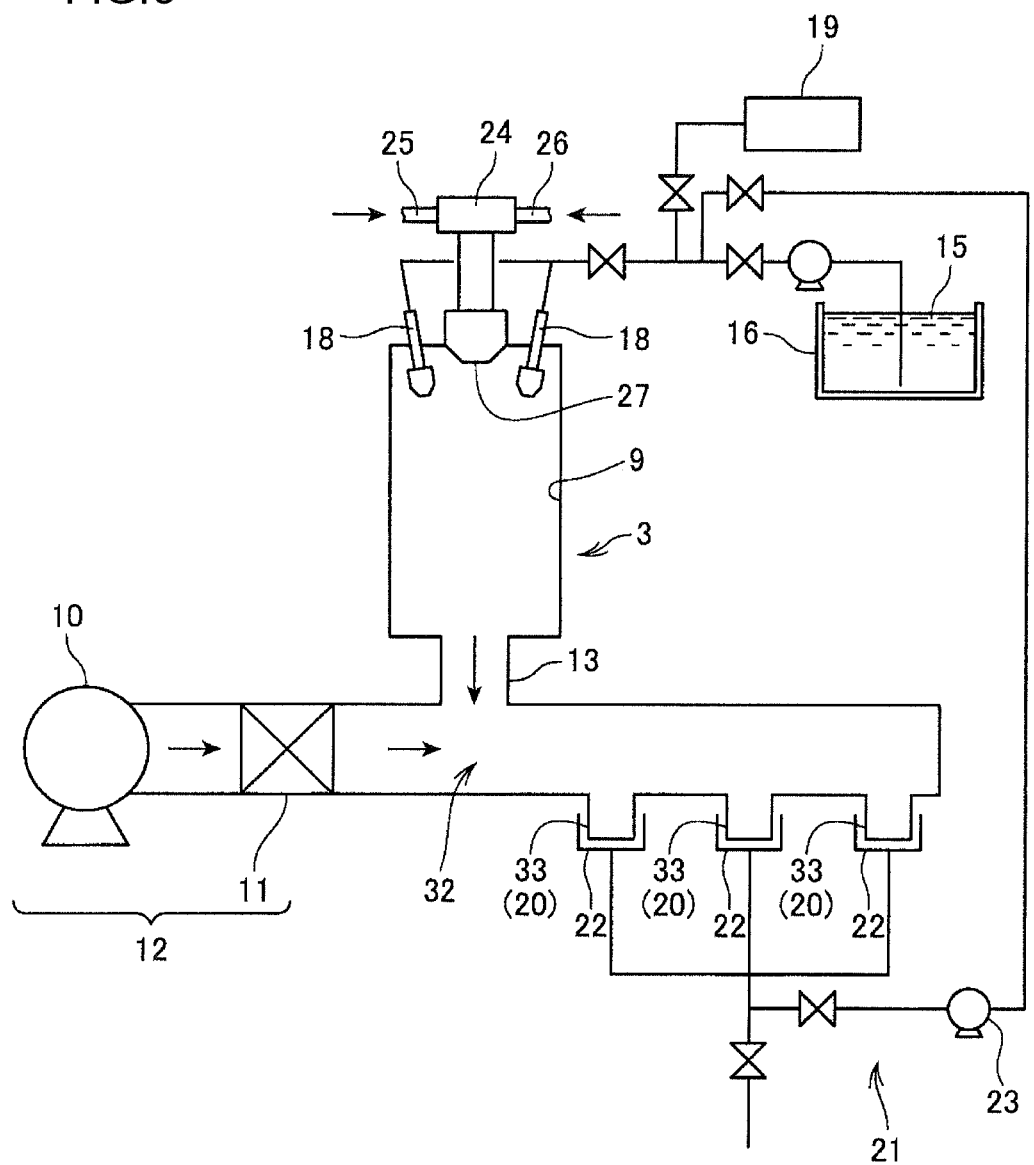
FIG. 6 is a side view illustrating the gasifier for a sterilizer of the third embodiment including a cleaning liquid circulating device according to the present invention.

The cleaning liquid 15 which is discharged from the sterilizer gas blowing port 33 which also functions as the cleaning liquid discharge port 20 may be directly discarded. However, as illustrated in FIG. 6, the cleaning liquid circulating device 21 can be provided as in the first embodiment, so that the cleaning liquid 15 which is blasted to the heating surface 9 can be recovered and the recovered cleaning liquid 15 can also be blasted to the heating surface 9. The cleaning liquid circulating device 21 includes the discharge port closing cup 22 for closing the sterilizer gas blowing port 33 which is the cleaning liquid discharge port 20, and recovering the cleaning liquid 15, and the circulation pump 23 that circulates the recovered cleaning liquid 15.

The sterilizer gas blowing port 33 which is the cleaning liquid discharge port 20 is closed with the discharge port closing cup 22, all of the cleaning liquid 15 which is discharged is recovered and is pressurized by the circulation pump 23, and the recovered cleaning liquid 15 is introduced into the flow path for the cleaning liquid 15. The introduced cleaning liquid 15 is blasted to the heating surface 9 again by the cleaning liquid blasting device 18. In this case, the recovered cleaning liquid 15 may be introduced into the cleaning liquid tank 16, and after the recovered cleaning liquid 15 is stored in the cleaning liquid tank 16, the recovered cleaning liquid 15 may be supplied to the cleaning liquid blasting device 18.

After the cleaning liquid 15 which is recovered by the cleaning liquid circulating device 21 is blasted to the heating surface 9, it is necessary to blast water or aseptic water to the heating surface 9 as the cleaning liquid 15, detach the discharge port closing cup 22 from the sterilizer gas blowing port 33, and discard the cleaning liquid 15. This is for removing the stabilizer, the acidic compound or the basic compound, and the other additives from the inside of the sterilizer evaporating portion 3. Further, during an operation, the gas of the sterilizer 4 is blown to packaging from the sterilizer gas blowing port 33, and therefore the discharge port closing cup 22 is detached, and is held so as not to interfere with the operation.

Although in the third embodiment, the cleaning liquid 15 is blasted to the heating surface 9 from the cleaning liquid blasting device 18 as in the second embodiment, the cleaning liquid 15 may be supplied to the spraying device 24 from the sterilizer supply port 25, and the cleaning liquid 15 may be blasted into the sterilizer evaporating portion 3 from the spray nozzle 27.

EXAMPLE

Hereinafter, the present invention will be described based on examples.

Operation Method

The gasifier 1 for a sterilizer illustrated in the second embodiment was used. Here, SUS316L was adopted as the material of the heating body 8 on the inner surface of the sterilizer evaporating portion 3, and the heating surface 9 is made of the same material as the heating body 8. As the sterilizer 4, a hydrogen peroxide solution containing 35% by mass of hydrogen peroxide and a stabilizer was supplied at 65 g/min to the sterilizer supply port 25 of the spraying device 24 which is a twin-fluid sprayer. Further, compressed air of 0.5 MPa was supplied to the compressed air supply port 26. The temperature of the heating body 8 was set at 300° C. The gasifier 1 for a sterilizer was operated for 24 hours under the above described conditions, and thereafter, cleaning as follows was conducted.

After the operation of the gasifier 1 for a sterilizer was stopped, and the temperature of the heating body 8 decreases to 150° C. or less, pressure of 0.2 MPa was added by the pump 17, and aseptic water was blasted to the heating surface 9 in the sterilizer evaporating portion 3 from the two cleaning liquid blasting devices 18 for 60 seconds. The blasting was stopped for 60 seconds, and blasting was further conducted for 60 seconds. This was repeated five times. Thereafter, air under pressure of 0.5 MPa was blasted into the sterilizer evaporating portion 3 from the two cleaning liquid blasting devices 18 for three minutes. Then, the heating body 8 was increased in temperature, and after the temperature of the heating body 8 reaches 300° C., the sterilizer 4 was sprayed from the spraying device 24 for 10 minutes. Thereafter, the operation of the gasifier 1 for a sterilizer was restarted. The operation was conducted for 300 days, and then the inner surface of the sterilizer evaporating portion 3 was observed. The example shows the case where cleaning was repeatedly conducted, whereas a comparative example shows a case where the gasifier 1 for a sterilizer was operated continuously without conducting cleaning even once.

According to the above described example, by cleaning the heating surface 9 of the gasifier 1 for a sterilizer, the stabilizer did not adhere to the heating surface 9 after the operation for a long time period, and accumulation of the stabilizer was able to be prevented. On the other hand, in the comparative example where cleaning was not conducted, accumulation of the stabilizer was confirmed.

According to the present invention, the gasifier 1 for a sterilizer was able to exhibit stable gasifying performance of the sterilizer 4 for a long time period without having accumulation of the stabilizer on the heating surface 9, and without losing heat conductivity from the heating body 8 to the heating surface 9. Further, the stabilizer no longer condenses to be a solid to enter packaging.

Although the present invention is configured as described above, the present invention is not limited to the above described embodiments, but can be variously changed within the gist of the present invention.

For example, when the heating body 8 of the gasifier 1 for a sterilizer is heated by an electric heating device, accumulation of the stabilizer onto the heating surface 9 is assumed to occur as a heating current value decreases. Therefore, the current output value may be monitored, and the value may be automatically reflected in cleaning parameters such as the blasting time period of the cleaning liquid 15 and the temperature of the heating body 8. Further, a hydrogen peroxide gas concentration measuring instrument may be provided in the blowing port 13 of the gasifier 1 for a sterilizer, the gasifying state of the gasifier 1 for a sterilizer may be monitored, and the gasifying state may be automatically reflected in the cleaning parameters such as the blasting time period of the cleaning liquid 15 and the temperature of the heating body 8.

REFERENCE SIGNS LIST

1 gasifier for sterilizer
2 sterilizer supplying portion
14 cleaning device
15 cleaning liquid
18 cleaning liquid blasting device
19 air supplying device
21 cleaning liquid circulating device

The invention claimed is:

1. A cleaning method of a gasifier for a sterilizer that brings a sterilizer containing at least hydrogen peroxide and a stabilizer into contact with a heating surface to gasify the sterilizer,
   wherein the heating surface is cleaned by blasting a cleaning liquid to the heating surface, a cleaning liquid blasting device that blasts the cleaning liquid is separate from a spray nozzle that sprays the sterilizer into the gasifier, and
   when the cleaning liquid is blasted to the heating surface the temperature of the heating surface is 50° C. to 250° C.

2. The cleaning method of a gasifier for a sterilizer according to claim 1,
   wherein after a product is produced by using an aseptic filling and packaging machine, the heating surface is cleaned by blasting a cleaning liquid to the heating surface.

3. The cleaning method of a gasifier for a sterilizer according to claim 2,
   wherein after the cleaning liquid is blasted to the heating surface, air is blasted to the heating surface.

4. The cleaning method of a gasifier for a sterilizer according to claim 3,
   wherein the cleaning liquid is water or water containing an acidic compound or a basic compound.

5. The cleaning method of a gasifier for a sterilizer according to claim 2,
   wherein the cleaning liquid is water or water containing an acidic compound or a basic compound.

6. The cleaning method of a gasifier for a sterilizer according to claim 1,
   wherein after the cleaning liquid is blasted to the heating surface, air is blasted to the heating surface.

7. The cleaning method of a gasifier for a sterilizer according to claim 6,
   wherein the cleaning liquid is water or water containing an acidic compound or a basic compound.

8. The cleaning method of a gasifier for a sterilizer according to claim 1,
   wherein the cleaning liquid is water or water containing an acidic compound or a basic compound.

* * * * *